United States Patent
Karg et al.

(10) Patent No.: US 10,660,318 B2
(45) Date of Patent: May 26, 2020

(54) NON-MAMMALIAN RAS TRANSGENIC ANIMAL MODEL

(71) Applicant: Tosk, Inc., Mountain View, CA (US)

(72) Inventors: Travis Karg, Santa Cruz, CA (US); William A. Garland, San Clemente, CA (US); Steve Yanofsky, Sunnyvale, CA (US)

(73) Assignee: Tosk, Inc., Mountain View, CA (US)

( * ) Notice: Subject to any disclaimer, the term of this patent is extended or adjusted under 35 U.S.C. 154(b) by 0 days.

(21) Appl. No.: 14/911,101

(22) PCT Filed: Aug. 19, 2014

(86) PCT No.: PCT/US2014/051746
§ 371 (c)(1),
(2) Date: Feb. 9, 2016

(87) PCT Pub. No.: WO2015/026860
PCT Pub. Date: Feb. 26, 2015

(65) Prior Publication Data
US 2016/0249593 A1    Sep. 1, 2016

Related U.S. Application Data

(60) Provisional application No. 61/867,979, filed on Aug. 20, 2013.

(51) Int. Cl.
*A01K 67/033*      (2006.01)
*A61K 49/00*       (2006.01)

(52) U.S. Cl.
CPC ...... *A01K 67/0339* (2013.01); *A61K 49/0008* (2013.01); *A01K 2217/052* (2013.01); *A01K 2227/706* (2013.01); *A01K 2267/0331* (2013.01)

(58) Field of Classification Search
CPC ........ A01K 67/0339; A01K 2267/0331; A01K 2227/706; A01K 2217/052; A61K 49/0008

USPC ................................................ 800/13, 3, 10
See application file for complete search history.

(56) References Cited

U.S. PATENT DOCUMENTS

2002/0174446 A1    11/2002    Cohen et al.
2013/0023420 A1    1/2013     Thomas et al.

FOREIGN PATENT DOCUMENTS

| WO | WO2001010204 A1 |   | 2/2001 |
| WO | WO 2005/035729  | * | 4/2005 |
| WO | WO2005035729 A2 |   | 4/2005 |
| WO | WO2009008837 A1 |   | 1/2009 |
| WO | WO2009055461 A1 |   | 4/2009 |
| WO | WO2013106683 A1 |   | 7/2013 |

OTHER PUBLICATIONS

Davison et al. (2008) Methods in Enzymology, vol. 438, 391-417.*
Wu et al. (2009) BMC Developmental Biology, vol. 9:53, pp. 1-11.*
Pandey et al. (2011) Pharmacol. Rev., vol. 63(2), 411-436.*
Prober et al. (2000) Cell, vol. 100, 435-446.*
Karim et al., Ectopic expression of activated Ras1 induces hyperplastic growth and increased cell death in *Drosophila* imaginal tissues, Development Jan. 1998;125(1):1-9.
Bishop et al., Expression of an activated ras gene causes developmental abnormalities in transgenic *Drosophila* melanogaster, Genes Dev. May 1988;2(5):567-77.
Davison et al., Characterization of Kras-mediated pancreatic tumorigenesis in zebrafish, Methods Enzymol. 2008;438:391-417.

* cited by examiner

*Primary Examiner* — Anne Marie S Wehbe
(74) *Attorney, Agent, or Firm* — Bret E. Field; Bozicevic, Field & Francis LLP (57) ABSTRACT

Non-mammalian, transgenic animals, e.g., flies, that include a RAS transgene, are provided. Also provided are methods of using the subject transgenic non-mammalian animals to identify compounds having activity with respect to cellular proliferative, such as neoplastic, diseases.

10 Claims, 8 Drawing Sheets

FIG. 1

Isoform 1

```
         10         20         30         40         50         60
MTEYKLVVVG AGGVGKSALT IQLIQNHFVD EYDPTIEDSY RKQVVIDGET CLLDILDTAG
         70         80         90        100        110        120
QEEYSAMRDQ YMRTGEGFLC VFAINNTKSF EDIHHYREQI KRVKDSEDVP MVLVGNKCDL
        130        140        150        160        170        180
PSRTVDTKQA QDLARSYGIP FIETSAKTRQ RVEDAFYTLV REIRQYRLKK ISKEEKTPGC
        190
VKIKKCIIM (SEQ ID NO:01)
```

Isoform 2

```
         10         20         30         40         50         60
MTEYKLVVVG AGGVGKSALT IQLIQNHFVD EYDPTIEDSY RKQVVIDGET CLLDILDTAG
         70         80         90        100        110        120
QEEYSAMRDQ YMRTGEGFLC VFAINNTKSF EDIHHYREQI KRVKDSEDVP MVLVGNKCDL
        130        140        150        160        170        180
PSRTVDTKQA QDLARSYGIP FIETSAKTRQ GVDDAFYTLV REIRKHKEKM SKDGKKKKKK
        190
SKTKCVIM (SEQ ID NO:02)
```

Mutations in Colorectal and Oral Cancer:

- G12→V12 and less often S12, C12, D12 or A12
- G13→D13
- Q61→L61

Mutations Associated with Resistance to Agents that Block EGF Signaling:

- G12→V12 and less often S12, C12, D12 or A12
- G13→D13
- Q61→L61

```
         10         20         30         40         50
 60
agatctacca tgactgaata taaacttgtg gtagttggag ctgttggcgt
aggcaagagt
         70         80         90        100        110
120
gccttgacga tacagctaat tcagaatcat tttgtggacg aatatgatcc
aacaatagag
        130        140        150        160        170
180
gattcctaca ggaagcaagt agtaattgat ggagaaacct gtctcttgga
tattctcgac
        190        200        210        220        230
240
acagcaggtc aagaggagta cagtgcaatg agggaccagt acatgaggac
tggggagggc
        250        260        270        280        290
300
tttctttgtg tatttgccat aaataatact aaatcatttg aagatattca
ccattataga
        310        320        330        340        350
360
gaacaaatta aaagagttaa ggactctgaa gatgtaccta tggtcctagt
aggaaataaa
        370        380        390        400        410
420
tgtgatttgc cttctagaac agtagacaca aaacaggctc aggacttagc
aagaagttat
        430        440        450        460        470
480
ggaattcctt ttattgaaac atcagcaaag acaagacagg gtgttgatga
tgccttctat
        490        500        510        520
aaaaagaagt caaagacaaa gtgtgtaatt atgtaactcg ag
```
(SEQ ID NO:03)

Grey Boxes=Restriction Sites
Un-shaded Box=Spacer
Black Box=12V Mutation Site

NON-MAMMALIAN RAS TRANSGENIC ANIMAL MODEL

CROSS-REFERENCE TO RELATED APPLICATIONS

Pursuant to 35 U.S.C. § 119 (e), this application claims priority to the filing date of U.S. Provisional Patent Application Ser. No. 61/867,979 filed Aug. 20, 2013; the disclosure of which application is herein incorporated by reference.

INTRODUCTION

Figure 1:
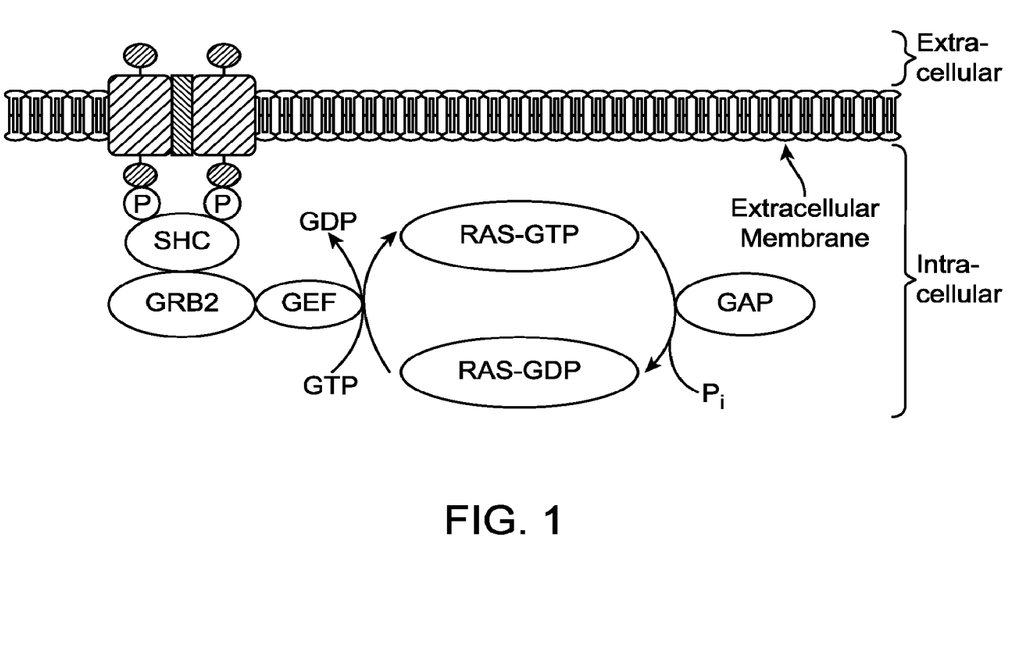
FIG. 1. Signaling pathway for RAS. Tyrosine kinases associated with activated growth factor receptors undergo autophosphorylation and interact with the adaptor proteins SHC and GRB2. These proteins associate with various GEFs which exchange GDP for GTP, thereby activating the RAS protein. GAPs stimulate the RAS protein's intrinsic GTPase activity, causing the hydrolysis of GTP to GDP, thereby inactivating the protein.

The RAS (rat sarcoma) proteins are a family of low molecular weight, GTP-binding/GTPases that play a role in regulating cell differentiation, proliferation and survival. (Wennerberg; et al., "The RAS superfamily at a glance", J. Cell Sci. (2005) 118: 843-846., Adjei, "Blocking oncogenic RAS signaling for cancer therapy", J. Natl. Cancer. Inst. (2001) 93:1062-1074.) There are three principal members of the RAS family: hRAS, nRAS, and kRAS. All members promote cancer formation and progression. (Kamoub; et al., "RAS oncogenes: split personalities", Nat. Rev. Mol. Cell Biol. (2008) 9:517-531.) The proposed signaling pathway for the RAS system is provided in FIG. 1. Note that the initiation of signaling by activation of tyrosine kinases is associated with various membrane-bound growth factors. Virtually all of these growth factors, e.g., EGF, are important to the growth of tumors.

Figure 2:
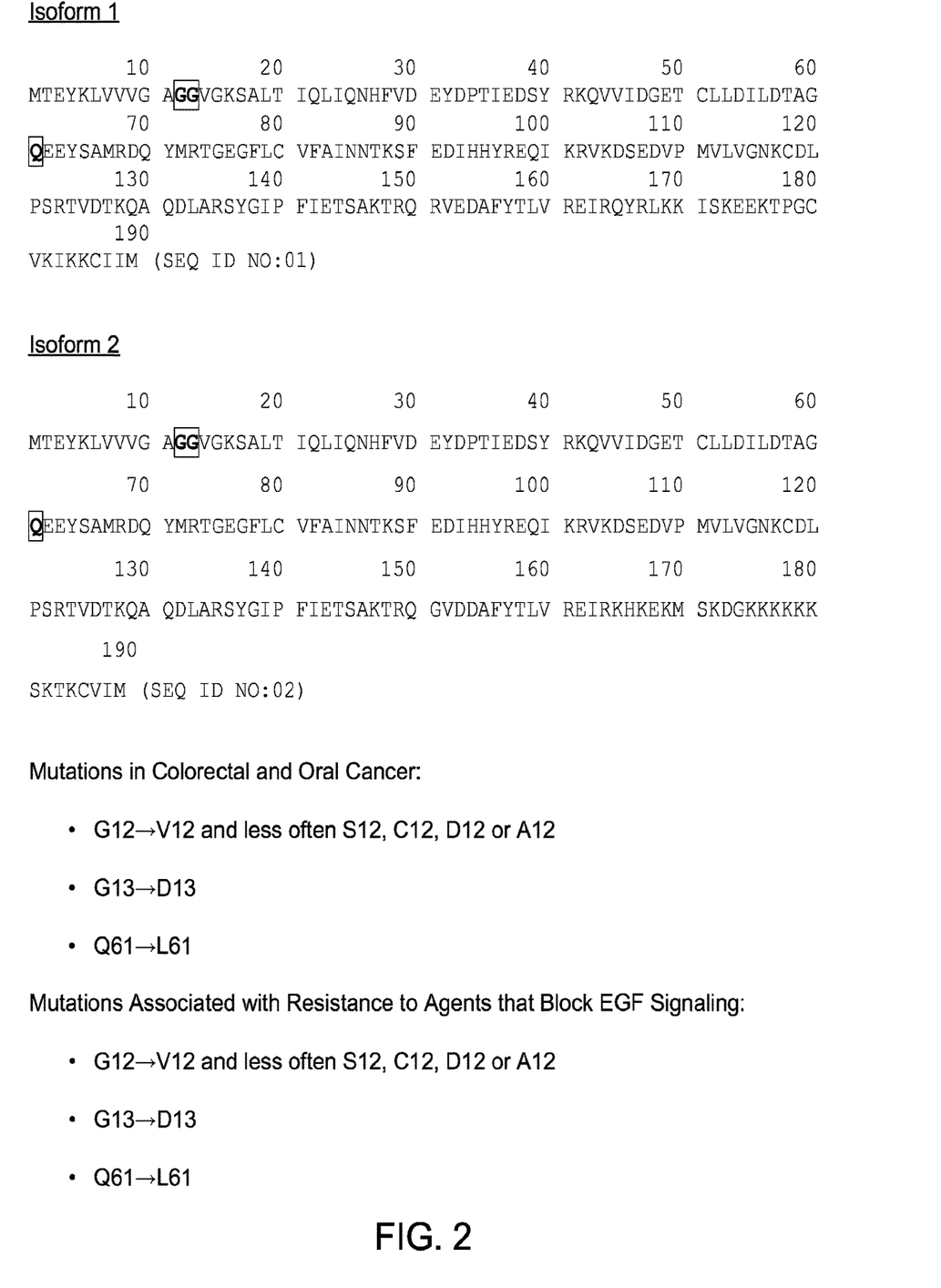
FIG. 2. The sequence of human kRAS with main sites of mutation noted.

Mutations in RAS are found in approximately 30% of human cancers. The sequence of human kRAS with the chief mutation sites noted is provided in FIG. 2. In the absence of a RAS mutation, increased RAS activity in human tumors has been shown to be the result of gene amplification or increased upstream activation. (Friday; et al., "K-RAS as a target for cancer therapy", Biochim. Biophys. Acta (2005) 1756:127-144). Single point mutations of the RAS gene, affecting residues G12 (G12V) and G13 (G13D), abolish GAP-induced GTP hydrolysis through steric hindrance, while Q61L mutations interfere with the coordination of a water molecule necessary for GTP hydrolysis. (Pylayeva-Gupta; et al., "RAS oncogenes: Weaving a tumorigenic web", Nat. Rev., Cancer (2011) 11:761-774). These mutations render the protein constitutively active, and the persistence of active GTP-bound RAS leads to the constant activation of its downstream effector pathways.

kRAS is the most frequently mutated RAS isoform and one of the proteins most frequently found mutated with cancer. For example, it is mutated in 90% of pancreatic adenocarcinomas, 45% of colorectal cancers and 35% of lung adenocarcinomas. (Downward, "Targeting RAS signalling pathways in cancer therapy", Nat. Rev. Cancer (2003) 3:11-22.) kRAS mutations are associated with increased tumorigenicity and poor prognosis. Additionally, the inhibition of activated RAS reverts malignant cells to a nonmalignant phenotype with concomitant tumor regression both in vitro and in vivo. (Podsypanina; et al., "Oncogene cooperation in tumor maintenance and tumor recurrence in mouse mammary tumors induced by Myc and mutant kRAS", Proc. Natl. Acad. Sci. U.S.A. (2008) 105: 5242-5247., Chin; et al., "Essential role for oncogenic RAS in tumour maintenance", Nature 1999; 400: 468-472.)

kRAS is an attractive therapeutic target for various cancers because of the frequent involvement of the RAS proteins, including kRAS, in the onset and progression of cancer. Efficient inhibition of oncogenic RAS signaling is considered even now the "Holy Grail" of cancer research. (Spiegel; et al., Small-molecule modulation of Ras signaling. Nat Chem Biol. (2014) 10:613-22). While the development of a small molecule inhibitor of the constitutively active kRAS protein would be ideal as a cancer therapeutic, 25 years of work on drugs targeting the GTP binding pocket of mutant kRAS has not yielded a successful molecule. (Vasan; et al., "A RAS Renaissance: Emerging Targeted Therapies for kRAS-Mutated Non-Small Cell Lung Cancer", Clin Cancer Res. (2014) 20:3921-3930.) To date, no effective therapy that specifically targets mutant kRAS is available. Targeting the constitutively active molecular switch of kRAS is quite difficult because the role of GDP or GTP is to stabilize the inactive or active states of the RAS protein. (Gysin; et al., "Therapeutic strategies for targeting RAS proteins", Genes Cancer (2011) 2:359-372.) This situation is unlike protein kinases in which phosphoryl transfer from ATP to a substrate is a rapid, catalytic process. Additionally, a competitive inhibitor is not likely to be found because of the pM affinity between kRAS and GTP, as well as the micromolar concentration of GTP in the cell. Furthermore, kRAS activation and signaling are accomplished through protein-protein interactions (PPIs) with guanine nucleotide exchange factors (GEFs), GTPase activating proteins (GAPs), and the various kRAS effector proteins. (Sun; et al., "Discovery of small molecules that bind to K-RAS and inhibit SOS-mediated activation", Angew. Chem., Int. Ed. (2012) 51:6140-6143.) PPIs are challenging to target because of the featureless topologies of the surfaces involved. (Fletcher et al., "Targeting protein-protein interactions by rational design: mimicry of protein surfaces", J. R. Soc. Interface (2006) 3:215-233.) Given the complexity of the kRAS system, it is not surprising that attempts to target aberrant kRAS signaling using various direct, and even virtually all indirect, approaches have failed.

Figure 3:
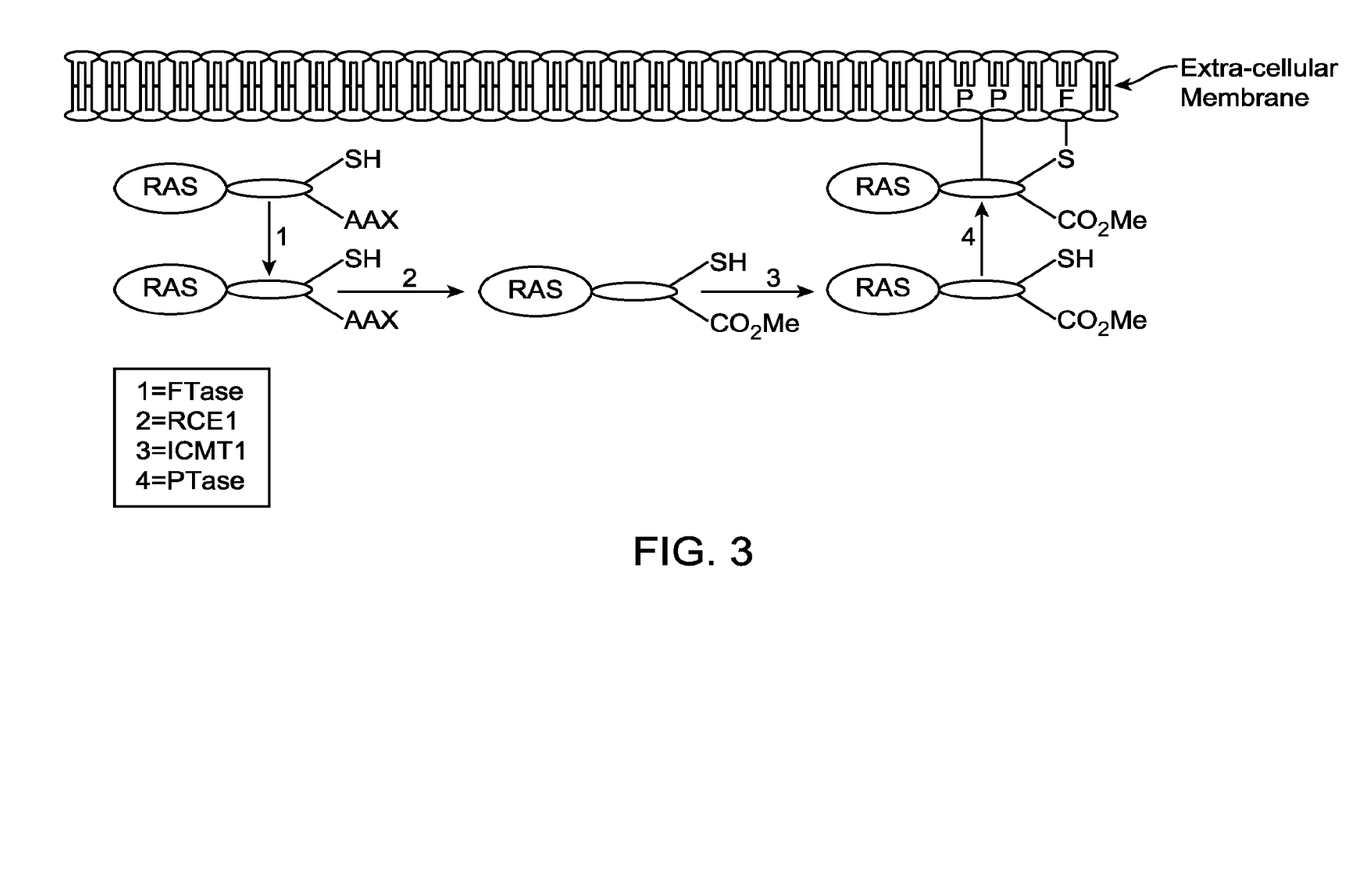
FIG. 3. Post-translational processing of RAS proteins. Farnesyltransferase (FTase) catalyzes the transfer of a farnesyl group to the terminal cysteine of new synthesized RAS proteins. Next, the three C-terminal amino acids are cleaved by the endopeptidase RAS-converting enzyme 1 (RCE1). Carboxymethylation of the terminal cysteine residue is accomplished by isoprenylcysteine carboxylmethyltransferase I (ICMT I). Finally, palmitoyl transferase (PTase) transfers a palmitoyl group to C-terminal cysteine residues of HRAS, NRAS, and the kRAS-4A isoform.

After RAS proteins are translated, they must undergo the series of post-translational modifications shown in FIG. 3. (Ghobrial; et al., "Inhibitors of the RAS oncogene as therapeutic targets", Hematol. Oncol. Clin. North Am. (2002) 16:1065-1088., Adjei, "FarnesyltransfeRASe inhibitors", Cancer Chemother. Biol. Response Modif. (2001) 19:149-164., Cho; et al., "Chemistry and biology of RAS farnesyi-transfeRASe", Arch. Pharm. Res. (2002) 25:759-769.) Initially, the thiol group of the terminal cysteine in kRAS is farnesylated by farnesyltransferase (FTase). (Casey; et al., "p21RAS is modified by a farnesyl isoprenoid", Proc. Natl. Acad. Sci. U.S.A. (1989) 86: 8323-8327., Cox; et al., "FarnesyltransfeRASe inhibitors and cancer treatment: targeting simply RAS?", Biochim. Biophys. Acta (1997) 1333: F51-F71., Hancock; et al., "All RAS proteins are polyisoprenylated but only some are palmitoylated" Cell (1989) 57, 1167-1177., Hancock; et al., "A polybasic domain or palmitoylation is required in addition to the CAAX motif to localize p21RAS to the plasma membrane", Cell (1990) 63:133-139.) Next, the CAAX (C=cysteine; A=isoleucine; X=serine or methionine) (Boyartchuk; et al., "Modulation of RAS and a-factor function by carboxyl-terminal proteolysis", Science (1997) 275:1796-1800., Otto; et al., "Cloning and characterization of a mammalian prenyl protein-specific protease", J. Biol. Chem. (1999) 274:8379-8382.) protease RAS-converting enzyme 1 (RCE1) cleaves the terminal AAX amino acids, and the carboxy group of the cysteine is methylated by isoprenylcysteine carboxylmethyltransferase I (ICMT I). (Clarke; et al., "Posttranslational modification of the Ha-RAS oncogene protein: evidence for a third class of protein carboxyl methyltransfeRASes", Proc. Natl. Acad. Sci. U.S.A. (1988) 85:4643-4647., Hrycyna; et al., "The

*Saccharomyces cerevisiae* STE14 gene encodes a methyltransfeRASe that mediates C-terminal methylation of a-factor and RAS proteins", EMBO J. (1991) 10:1699-1709., Dal; et al., "Mammalian prenylcysteine carboxylmethyltransfeRASe is in the endoplasmic reticulum", J. Biol. Chem. (1998) 273: 15030-15034.) Finally, palmitoyl transferase (PTase) transfers a palmitoyl moiety to cysteine residues located just upstream of the C-terminus of hRAS, nRAS and kRAS. The RAS protein then forms a stable interaction with the cell membrane via its farnesyl and palmitoyl groups as well as the positively charged C-terminal lysine residues.

The post-translational, downstream modification of kRAS offers several possible drug targets: farnesyltransferase inhibitors (FTase), (Appels; et al., "Development of farnesyl transfeRASe inhibitors: a review", Oncologist (2005) 10: 565-578.) CAAX endopeptidase, (Wright; et al., "Thematic review series: lipid posttranslational modifications. CAAX modification and membrane targeting of RAS", J. Lipid Res. (2006) 47:883-891., Manandhar; et al., "Chemical inhibition of CaaX protease activity disrupts yeast RAS localization", Yeast (2010) 27:327-343.) methyltransferase, (Winter-Vann; et al., "A small-molecule inhibitor of isoprenylcysteine carboxyl methyltransfeRASe with antitumor activity in cancer cells", Proc. Natl. Acad. Sci. U.S.A. (2005) 102:4336-4341.) or palmitoyl transferase. FTase inhibitors have been studied most extensively as modulators of kRAS activity. FTAse inhibitors (Sebti; et al., "Farnesyltransferase and geranylgeranytransferase I inhibitors and cancer therapy: lessons from mechanism and bench-to-bedside translational studies", Oncogene (2000) 9:6584-6593., Cox; et al., "Farnesyltransferase inhibitors: promises and realities", Curr. Opin. Pharmacol. (2002) 2:388-393.) fall into two categories: the CAAX peptidomimetics, including FTI-276, (Sun; et al., "Both farnesyltransferase and geranyigeranyltransferase I inhibitors are required for inhibition of oncogenic K-Ras prenylaton but each alone is sufficient to suppress human tumor growth in nude mouse xenografts", Oncogene (1998) 16:1467-1473.) FTI-277, (Lerner; et al., "Ras CAAX peptidomimetic FTI-277 selectively blocks oncogenic Ras signaling by inducing cytoplasmic accumulation of inactive Ras-Raf complexes", J. Biol. Chem. (1995) 270:26802-26806.) L-744832, (Song; et al., "K-Ras-independent effects of the farnesyl transferase inhibitor L-744,832 on cyclin B1/Cdc2 kinase activity, G2/M cell cycle progression and apoptosis in human pancreatic ductal adenocarcinoma cells", Neoplasia (2000) 2: 261-272.), B956 (Nagasu; et al., "Inhibition of human tumor xenograft growth by treatment with the farnesyl transferase inhibitor B956", Cancer Res. (1995) 55, 5310-5314.) and FTI-2153, (Crespo; et al., "The farnesyltransferase inhibitor, FTI-2153, blocks bipolar spindle formation and chromosome alignment and causes prometaphase accumulation during mitosis of human lung cancer cells", J. Biol. Chem. (2001) 276: 16161-16167.) and the nonpeptidomimetics, which include tipifarnib (Beaupre; et al. "R115777 Induces Ras-independent apoptosis of myeloma cells via multiple intrinsic pathways.", Mol. Cancer Ther. (2004) 3: 179-186.) lonafarnib (Wang; et al., "The farnesyl protein transferase inhibitor lonafarnib (SCH66336) is an inhibitor of multidrug resistance proteins 1 and 2", Chemotherapy (2003) 49:303-308.) and BMS-214662. (Rose; et al. "Preclinical antitumor activity of BMS-214662.; a highly apoptotic and novel farnesyltransferase inhibitor", Cancer Res. (2001) 61, 7507-7517.) A number of recent publications describe their preclinical efficacy. (Haluska; et al., "Farnesyl transferase inhibitors as anticancer agents", Eur. J. Cancer (2002) 38, 1685-1700., Sebti, "Blocked pathways: FTIs shut down oncogene signals", Oncologist (2003) 8 (Suppl. 3): 30-38.) However, none of these agents appear to be advancing toward approval to market.

Upstream targets for kRAS inhibition include tyrosine kinases, (Sawyers., "Rational therapeutic intervention in cancer: kinases as drug targets", Curr. Opin. Genet. Dev. (2002) 12:111-115.) the GRB2/GEF interaction (Qulliam; et al., "Membrane-targeting potentiates guanine nucleotide exchange factor CDC25 and SOS1 activation of RAS transforming activity", Proc. Natl. Acad. Sci. U.S.A. (1994); 91: 8512-8516.) and GEFs. (Shields; et al., "Understanding RAS: "it ain't over 'til it's over".", Trends Cell Biol. (2000) 10; 147-154.)

RAS proteins cycle between the inactive GDP-bound form and the active GTP-bound form. This activation state is regulated by GEFs and GAPs (FIG. 3). (Reuther; et al., "The RAS branch of small GTPases: RAS family members don't fall far from the tree", Curr. Opin. Cell Biol. (2000) 12:157-165., Takai; et al., "Small GTP-binding proteins. Physiol. Rev. (2001) 81:153-208., Cullen; et al. "Integration of calcium and RAS signaling", Nat. Rev. Mol. Cell Biol. (2002); 3:339-348., Heldin, "Dimerization of cell surface receptors in signal transduction", Cell (1995) 80:213-223., Lemmon; et al., "Regulation of signal transduction and signal diversity by receptor oligomerization", Trends Biochem. Sci. (1994) 19:459-463., Weiss; et al., "Novel mechanisms of RTK signal generation", Curr. Opin. Genet. Dev. (1997) 7: 80-86.) When a growth factor binds to a tyrosine kinase receptor, it forms an active homodimer that undergoes auto-phosphorylation. This leads to binding of the adaptor proteins SHC and growth factor receptor bound 2(GRB2). GRB2 then associates with GEFs through its SH3 domain. GEFs exchange bound GDP for GTP, thereby activating the RAS protein and initiating a signaling cascade. To terminate signaling, GAPs stimulate the intrinsic GTPase activity of RAS proteins, causing the hydrolysis of GTP to GDP, leading to deactivation of the RAS protein.

Figure 4:
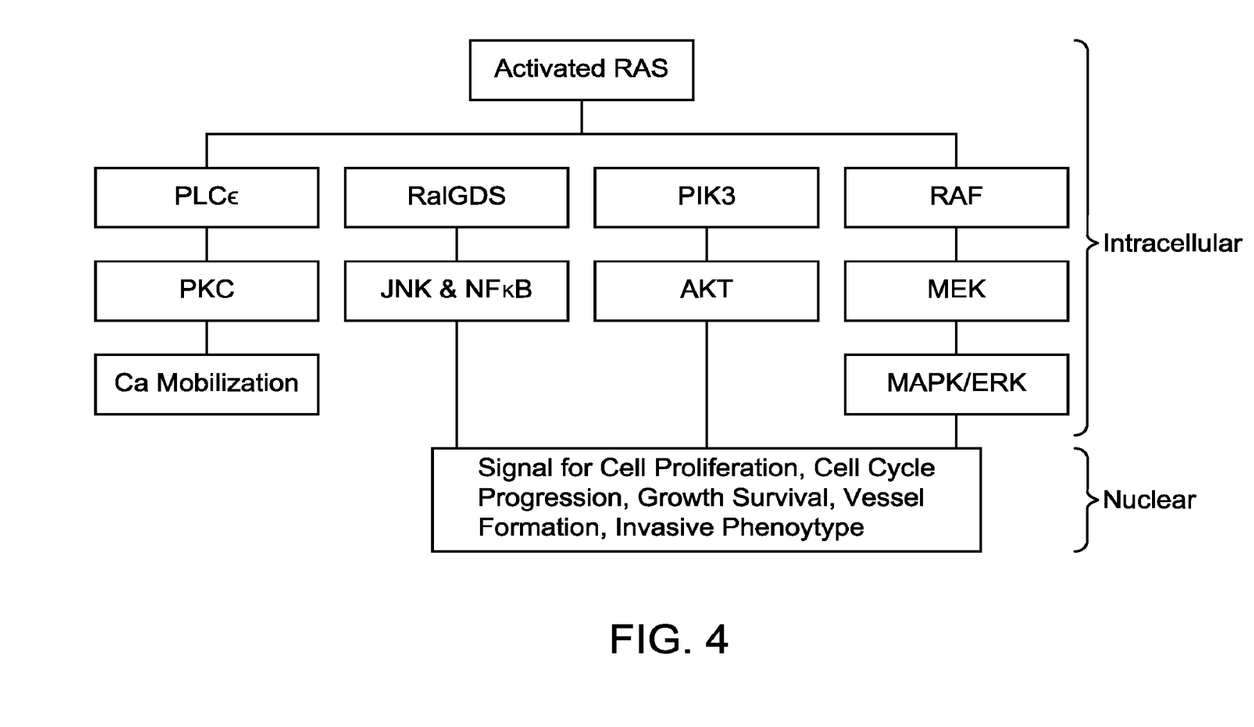
FIG. 4. Downstream signaling of RAS. RAS interacts with a number of downstream effectors. The main ones include RAF protein kinases, phosphoinositide 3-kinases (PI3Ks), guanine nucleotide exchange factors for the RAS-related protein Ral (RalGDS), and phospholipase Cε (PLCε).

Although protein-protein interactions such as RAS/GEF are notoriously difficult to modulate, several RAS-GEFs have been identified. Most research efforts have focused on the interaction of kRAS with a particular GEF, son of sevenless (SOS). The pockets adjacent to the kRAS/SOS contact surface are amenable to small-molecule binding, (Maurer; et al., "Small-moleculeligands bind to a distinct pocket in RAS and inhibit SOS-mediated nucleotide exchange activity", Proc. Natl. Acad. Sci. U.S.A. (2012) 109:5299-5304.) and NMR-based fragment screening recently identified small molecules that bind to the pocket adjacent to the kRAS/SOS interaction surface and subsequently interfered with the kRAS/SOS interaction. However, no drug candidates from this approach have been reported.

kRAS can interact with many downstream effector proteins to alter cell survival and proliferation (FIG. 4). (Schlessinger, "Cell signaling by receptor tyrosine kinases", Cell (2000) 103:211-225., Repasky; et al., "Renewing the conspiracy theory debate: does Raf function alone to mediate RAS oncogenesis?", Trends Cell Biol (2004) 14:639-647.) The main ones include RAF protein kinases, phosphoinositide 3-kinases (PI3Ks), guanine nucleotide exchange factors for the RAS-related protein Ral (RalGDS), and phospholipase Cε (PLCε). RAF initiates the mitogen-activated protein (MAP) kinase cascade, which activates extracellular signal-regulated kinase (ERK). This active kinase has numerous targets, Including the transcription factor ELK1, which regulates the expression of cell-cycle progression genes. (Leevers; et al., "Requirement for RAS in Raf activation is overcome by targeting Raf to the plasma membrane", Nature (1994) 369:411-414., Marais; et al., "RAS recruits Raf-1 to the plasma membrane for activation by tyrosine phosphorylation", EMBO J. (1995) 14:3136-3145., Finney; et al., "RAS-Raf complexes: analyses of complexes formed in vivo", Methods Enzymol. (1995) 255, 310-323. Johnson; et al., "Identification of key residues in the A-Raf kinase important for phosphoinositide lipid binding specificity", Biochemistry (2005) 44: 3432-3440., Ghosh; et al., "Functional analysis of a phosphatidic acid binding domain in human Raf-1 kinase: mutations in the phosphatidate binding domain lead to tail and trunk abnormalities in developing zebrafish embryos", J. Biol. Chem. (2003) 278: 45690-45696.) The PI3K pathway activates AKT and leads to the transcription of pro-survival genes, cytoskeletal remodeling, and the activation of numerous transcription-factor pathways, most notably NF-κB. (Rodriguez-Viciana; et al., "Phosphatidylinositol-3-OH kinase as a direct target of RAS", Nature (1994) 370: 527-532., Pacold; et al., "Crystal structure and functional analysis of RAS binding to its effector phosphoinositide 3-kinase y", Cell (2000) 103: 931-943.) The activation of the RAL1 binding protein leads the inhibition of FOX transcription factors (De Ruiter; et al., "Regulation of the Forkhead transcription factor AFX by Ral-dependent phosphorylation of threonines 447 and 451", Mol. Cell. Biol. (2001) 21: 8225-8235.) which are involved in cell growth, proliferation, and differentiation. RalGDS can also signal through the JNK pathway to stimulate the transcription of pro-survival and cell-cycle progression genes. (González-Garcia; et al., "RalGDS is required for tumor formation in a model of skin carcinogenesis", Cancer Cell (2005) 7, 219-226., Hofer; et al., "Activated RAS interacts with the Ral guanine nucleotide dissociation stimulator", Proc. Natl. Acad. Sci. U.S.A. (1994) 91:11089-11093.) The activation of PLCε results in protein kinase C (PKC) activation and the mobilization of calcium from intracellular stores.

These downstream effectors of kRAS represent some of the most important cancer targets currently under study in the pharmaceutical industry. The importance of these downstream targets of kRAS provides further evidence of the importance of kRAS in the development and spread of cancer.

In addition to the significant role of kRAS in promoting cancer, this GTPase also has a critical role in affecting the efficacy of a major class of anti-cancer drugs, those that inhibit the EGF pathway. As previously mentioned, kRAS is a major effector molecule in the EGFR downstream signaling cascade controlling the proliferation, differentiation, and survival of cells. kRAS transmits growth signals from the EGFR receptor to major signaling systems such as the MAPK and PI3K-AKT systems. Mutated kRAS allows the EGFR system to bypass the natural controls present in the EGF system and operate continuously locked in a pro-growth mode (wild-type kRAS is self-inactivating, while oncogenic kRAS is not self-Inactivating). Consistent with this mechanism, the presence of mutated kRAS predicts lack of response to anti-EGF monoclonal antibody drugs such as panitumumab (Vectibix®) or cetuximab (Erbitux®) used to treat colorectal and many other cancers. Indeed, the most reliable way to currently predict whether a colorectal cancer patient will respond to one of these popular EGFR-inhibiting drugs is to test for "activating" mutations in the gene that encodes kRAS. In this regard, the G12V mutation appears more significant as a predictor of lack of response to anti-EGF therapeutics than the G13D mutation. (Chen; et al., "Association between kRAS codon 13 mutations and clinical response to anti-EGFR treatment in patients with metastatic colorectal cancer: results from a meta-analysis", Cancer Chemother Pharmacol. (2013) 71: 265-72., Mao C; et al., "kRAS p.G13D mutation and codon 12 mutations are not created equal in predicting clinical outcomes of cetuximab in metastatic colorectal cancer: a systematic review and meta-analysis", Cancer. (2013) 119:714-721.)

In 2009, the FDA updated the labels for panitumumab and cetuximab to treat metastatic colorectal cancer to include information about inactivity with these agents with kRAS mutations. Therefore, a drug that targets the mutated forms of kRAS responsible for the inactivity of these drugs without affecting the normal form should restore the activity of anti-EGF drugs.

SUMMARY

Non-mammalian, transgenic animals, e.g., flies, that include a RAS transgene, are provided. Also provided are methods of using the subject transgenic non-mammalian animals to identify compounds having activity with respect to cellular proliferative, such as neoplastic, diseases.

DETAILED DESCRIPTION

Non-mammalian, transgenic animals, e.g., flies, that include a RAS transgene, are provided. Also provided are methods of using the subject transgenic non-mammalian animals to identify compounds having activity with respect to cellular proliferative, such as neoplastic, diseases.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating un-recited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are Incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Transgenic Animal Models

As summarized above, aspects of the invention include non-mammalian RAS transgenic animals. A number of different types of non-mammalian multi-cellular organisms may be employed in the subject methods, where these types of organisms include insects, amphibians, fish, and the like. Specific organisms of interest include, but are not limited to: *Xenopus*, Zebrafish, Caenerhabditis, *Drosophila* and the like. Of interest in certain embodiments are invertebrate animals, such as members of the phylum arthropoda, and including members of the class insecta. Of interest in certain embodiments are flies. In some instances, the flies are members of the family Drosophilidae, for example *Drosophila melanogaster*. The multi-cellular organisms employed in the subject invention may be at any stage of their life, e.g., in the larval stage, in the adult stage, etc.

Aspects of transgenic animals of interest is that the animals harbor a stably integrated RAS transgene. The term "transgene" is used herein to describe genetic material which has been or is about to be artificially inserted into the genome of a cell. As the Integrated transgene of the animals of Interest is a RAS transgene, the transgene Includes a ras nucleic acid coding sequence that encodes a RAS protein. In some instances, the RAS protein is hRAS, nRAS or kRAS. The encoded RAS protein is, in some instances, a mammalian RAS protein, e.g., a murine or human RAS protein.

In some Instances, the transgene encodes a variant of a wild-type RAS protein, where variants of interest include homologs, mutants, etc. In some instances, the encoded RAS protein is a RAS homolog. By homolog is meant a protein having at 10% or more, such as 20% or more and including 30% or more, e.g., 35% or more, 40% or more and including 60% or more amino acid sequence identity to a wild-type RAS protein, such as human kRAS having the sequence provided in FIG. 2, as determined using MegAlign, DNAstar (1998) clustal algorithm as described in D. G. Higgins and P. M. Sharp, "Fast and Sensitive multiple Sequence Alignments on a Microcomputer," (1989) CABIOS, 5: 151-153. (Parameters used are ktuple 1, gap penalty 3, window, 5 and diagonals saved 5). In some embodiments, homologues of interest have much higher sequence identity, e.g., 65%, 70%, 75%, 80%, 85%, 90% or higher. Also of interest are proteins that are substantially identical to the wild type protein, where by substantially identical is meant that the protein has an amino acid sequence identity to the sequence of wild type protein of 60% or more, such as 65% or more and including 70% or more, where in some instances the identity may be much higher, e.g., 75%, 80%, 85%, 90%, 95% or higher.

The RAS transgene may also encode a mutant RAS protein. Mutants may retain biological properties of the wild-type (e.g., naturally occurring) proteins, or may have biological properties which differ from the wild-type proteins. Mutants may vary, and may include single amino acid changes, insertions or deletions of one or more amino acids (which may or may not be contiguous), N-terminal truncations, C-terminal truncations, etc.

In some instances, the transgene encodes a mutant human kRAS protein that includes one or more amino acid substitution mutations. Substitution mutations of interest include G12 mutations, G13 mutations, and Q61 mutations. For example, the mutant protein may include a G12X mutation, wherein X is any amino acid other than G. Specific substitution mutations include, but are not limited to: G12V, G13D and Q61L.

In some instances, the RAS transgene manifests in the transgenic animal as an observable non-lethal phenotype in the adult stage of the animal. By non-lethal is meant that the adult is alive and exhibits the phenotype at least for a period of time sufficient for the phenotype to be observed, e.g., for 1 day or longer, 5 days or longer, 10 days or longer, etc. By observable phenotype is meant a phenotype that can be visually seen in the adult stage of the animal, and may be observed in any anatomical feature. For example, with flies, anatomical features include eyes, wings, legs, etc. Where the anatomical feature is an eye, observable phenotypes of Interest include, but are not limited to: rough edges, presence/absence, color, shape, rough edges, etc. etc. Where the anatomical feature is a wing, observable phenotypes of interest include, but are not limited to: crinkled wing, incomplete wing (wing missing one or more parts), etc.

The RAS transgene may be ubiquitously expressed or expressed in tissue specific manner, i.e., where the transgene is expressed in one or more tissues of the animal but not all tissues of the animal. For example, the transgene may be expressed solely in wing tissue, solely in eye tissue, etc. Furthermore, the transgene may be expressed in all life stages of the animal, or in one or more stages but not all life stages of the animal.

Where desired, the transgene may be stably integrated into the genome of the animal in manner such that its expression is controlled spatially to the desired cell type. Specifically, the subject transgene may be stably integrated into the genome of the animal under the control of a promoter that provides for expression in a tissue of interest, e.g., wing tissue. The transgene may be under the control of any convenient promoter that provides for this requisite spatial expression pattern, where the promoter may be endogenous or exogenous to the animal.

The transgene may be integrated into the fly genome in a manner that provides for direct or indirect expression activation by the promoter, i.e., In a manner that provides for either cis or trans activation of gene expression by the promoter. In other words, expression of the transgene may be mediated directly by the promoter, or through one or more transactivating agents. Where the transgene is under direct control of the promoter, i.e., the promoter regulates expression of the transgene in a cis fashion, the transgene is stably integrated into the genome of the fly at a site sufficiently proximal to the promoter and in frame with the promoter such that cis regulation by the promoter occurs.

In yet other embodiments where expression of the transgene is indirectly mediated by the endogenous promoter, the promoter controls expression of the transgene through one or more transactivating agents, usually one transactivating agent, i.e., an agent whose expression is directly controlled by the promoter and which binds to the region of the transgene in a manner sufficient to turn on expression of the transgene. Any convenient transactivator may be employed, where the GAL4 transactivator system is employed in certain embodiments.

In these embodiments in which the transgenic fly comprises the GAL4 targeted expression system, a GAL4 encoding sequence is stably integrated into the genome of the animal in a manner such that it is operatively linked to the endogenous promoter that provides for expression in the appropriate spatial and temporal manner. An example of such a fly is fly line MS1096 obtained from the Bloomington Stock Center (Bloomington, Ind. (stock number 8860). MS1096 expresses GAL4 in the Drosophila wing and therefore only drives expression of a UAS responsive kRAS transgene in the Drosophila wing. The transgene is stably integrated into a different location of the genome, generally a random location in the genome, where the transgene is operatively linked to an upstream activator sequence, i.e., UAS sequence, to which GAL4 binds and turns on expression of the transgene. Transgenic flies having a UAS: GAL4 transactivation system are known to those of skill in the art and are described in Brand & Perrimon, Development (1993) 118: 401-415; and Phelps & Brand, Methods (April 1998) 14:367-379.

The subject transgenic flies can be prepared using any convenient protocol that provides for stable integration of the transgene into the fly genome in a manner sufficient to provide for the desired expression of the transgene, for example in a ubiquitous or tissue specific, e.g., wing specific, manner. A number of different strategies can be employed to obtain the integration of the transgene with the requisite expression pattern. Generally, methods of producing the subject transgenic flies involve stable integration of the transgene into the fly genome. Stable integration is achieved by first introducing the transgene into a cell or cells of the fly, e.g. a fly embryo. The transgene is generally present on a suitable vector, such as a plasmid. Transgene introduction may be accomplished using any convenient protocol, where suitable protocols include: electroporation, microinjection, vesicle delivery, e.g. liposome delivery vehicles, and the like. Following Introduction of the transgene into the cell(s), the transgene is stably integrated into the genome of the cell. Stable integration may be either site specific or random, but is generally random.

Where integration is random, the transgene may be integrated with the use of transposase. In such embodiments, the transgene is introduced into the cell(s) within a vector that includes the requisite terminal 31 base pair inverted repeats. Where the cell into which the transgene is to be integrated does not comprise an endogenous transposase, a vector encoding a transposase is also introduced into the cell, e.g. a helper plasmid comprising a transposase gene, such as pTURBO (as disclosed in Steller & Pirrotta, "P Transposons Controlled by the Heat Shock Promoter," Mol. Cell. Biol. (1986) 6:1640-1649). Methods of random integration of transgenes into the genome of a target Drosophila melanogaster cell(s) are disclosed in U.S. Pat. Nos. 4,670,388 and 6,475,798, the disclosures of which are herein incorporated by reference.

In those embodiments in which the transgene is stably integrated in a random fashion into the fly genome, means are also provided for selectively expressing the transgene at the appropriate time during development of the fly. In other words, means are provided for obtaining targeted expression of the transgene. To obtain the desired targeted expression of the randomly integrated transgene, integration of particular promoter upstream of the transgene, as a single unit in the P element vector may be employed. Alternatively, a transactivator that mediates expression of the transgene may be employed. Of particular interest is the GAL4 system described in Brand & Perrimon, supra, e.g., as described above In certain embodiments, transgenic flies are produced by: (1) generating two separate lines of transgenic flies: (a) a first line that expresses GAL4 in a tissue specific manner, e.g., in wing tissue, such as described above; and (b) a second line in which the transgene is stably integrated into the cell genome and is fused to a UAS domain; (2) crossing the two lines; and (3) screening the progeny for the desired phenotype, i.e. spontaneous development of neoplastic tumors. Each of the above steps are well known to those of skill in the art. See e.g. Brand & Perrimon, Development (1993) 118: 401-415; and Phelps & Brand, Methods (April 1998) 14:367-379. See also the Experimental Section, Infra. In another embodiment, the methods described for the G12V genotype are used to produce kRAS mutant flies that expresses other commonly found kRAS mutants: G13D and Q61L. Besides flies containing a single mutations, in some embodiments flies with multiple mutations, e.g., G12V and G13DV, G12V and Q61L, G13DV and Q61L and even a fly containing all three mutations, are employed.

The above strategy is employed to obtain fertilized eggs that comprise the transgene stably integrated into the genome in a manner such that it is expressed in the correct spatial and temporal manner so that the eggs give rise to adult flies exhibiting the desired phenotype, e.g., crinkled wing phenotype. The fertilized eggs may be allowed to mature under conditions that give rise to the neoplastic phenotype.

The phenotype of the animals can be tailored by varying the conditions under which the animals are allowed to mature. For example, temperature can be employed to modulate the nature of the phenotype of the subject animals.

Utility

The subject animals find use in a variety of applications, including as a screening tool that identifies therapeutic compounds for use in the treatment of cellular proliferative conditions (e.g., as animal models for human neoplastic disease conditions). Through use of the subject transgenic animals, e.g., flies (or cells derived therefrom depending on the particular screening assay), one can identify compounds that have activity with respect to a neoplastic disease. Compounds have activity with respect to a neoplastic disease if they modulate or have an effect on at least one parameter or symptom of the disease, such as loss abnormal cell division or complications associated therewith, where the modulatory activity may be to reduce or enhance the magnitude of the symptom, depending on the nature of the disease and the symptom. Thus, the screening methods of subject invention can be used to identify compounds that modulate the progression of neoplastic diseases, e.g. by binding to, modulating, enhancing or repressing the activity of a protein or peptide involved in the progression of the neoplastic disease, and/or compounds that ameliorate, alleviate or even remove the phenotypic symptoms of the disease, where such activity may or may not be the result of activity with respect to the underlying mechanism of the disease. Screening to determine drugs that lack effect on the neoplastic condition is also of interest. Assays of the invention make it possible to Identify compounds which ultimately: (1) have a positive affect with respect to a neoplastic disease condition and as such are therapeutics, e.g. agents which arrest or reverse the neoplastic condition or ameliorate or alleviate the symptoms of such a condition; or (2) have an adverse affect with respect to the neoplastic disease and as such should be avoided as therapeutic agents.

In the screening methods of the subject invention, a quantity of a candidate agent is generally orally administered to the animal, e.g., fly. Following oral administration, the effect of the candidate agent on the observable phenotype (e.g., crimped wing) is determined, typically by comparison with a control (i.e. a transgenic fly to which the candidate agent has not been administered). The effect of the candidate agent is determined by determining whether one or more of the phenotypic characteristics of the neoplastic condition are exacerbated or ameliorated in the test fly as compared to the control fly, where characteristics that are monitored include crimped wing, and the like. The candidate agent may be orally administered to the fly by mixing the agent into the fly nutrient medium, e.g. water, aqueous solution with additional nutrient agents, etc., and placing the medium in the presence of the fly, (either the larva or adult fly) such that the fly feeds on the medium. Where desired, a plurality of assay mixtures may be run in parallel with different agent concentrations to obtain a differential response to the various concentrations of candidate agent. Conveniently, one of these concentrations serves as a negative control, i.e. no compound. In certain embodiments, a high throughput screening protocol is employed, in which a large number of candidate agents are tested in parallel using a large number of flies. By "large number" is meant a plurality, where plurality means 10 to 50 or more, such as 100 or more, and including 1000 or more, where the number of may be 10,000 or 50,000 or more, and in some instances 5000 or less.

Of interest in certain embodiments is the use of the subject files in a high throughput toxicity screening assays, e.g., as described in U.S. Pat. Nos. 6,855,504 and 6,365,129, the disclosures of which are herein incorporated by reference. In such high throughput screening assays, a plurality of different compound compositions, usually 10 or more different compound compositions, are simultaneously assayed for their activity, if any. Each compound composition in the plurality is assayed for activity by contacting it with a population of the subject transgenic animals having a phenotype and determining the effect of the compound composition on the animals. Such HTS methods find use in finding agents for use in the treatment of cellular proliferative diseases, e.g., neoplastic diseases, as only those compounds that treat the disease and yet are sufficiently non-toxic to allow the animal to live are identified as positives for further study.

The subject methods find use in the screening of a variety of different potentially therapeutic candidate agents. Candidate agents encompass numerous chemical classes, though typically they are organic molecules, including small organic compounds having a molecular weight of 50 or more and 2,500-2000 daltons or less. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to: peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. New potential therapeutic agents may also be created using methods such as rational drug design or computer modeling.

Screening may be directed to known pharmacologically active compounds and chemical analogs thereof, or to new agents with unknown properties such as those created through rational drug design. Candidate agents having therapeutic activity with respect to the neoplastic condition can be identified based on their ability to at least ameliorate, if not completely alleviate or remove, one or more of the neoplastic phenotypes of the adult transgenic fly of the subject invention, such as tumor growth, tumor metastasis, and the like, as described above.

Of interest in certain embodiments is the use of the subject screening methods to identify cancer therapeutic agents that exhibit low host toxicity and yet are effective as antineoplastic agents. Tradition chemotherapy and radiation treatments affect normal and tumor cells alike. The tolerance for normal cells is high because the primary mechanism of these treatments affect only dividing cells and since the majority of normal cells are not dividing the side effects are tolerated, but still quite severe. The subject screening methods place a high stringency on side effects as a significant amount of cell division is required for the larva to develop into a viable fly. Therefore the anti-metastatic tumor compounds selected by the subject screening methods will have to be highly specific to kill or inhibit tumor formation/growth/metastasis, otherwise the developing fly will die. In other words, the subject methods represent a sensitive system for selecting anti-tumor drug candidates that also have low toxicity to normal developing and dividing cells.

The above screening methods may be part of a multi-step screening process of evaluating candidate therapeutic agents for their efficacy (and safety) in the treatment of neoplastic diseases in mammalian hosts, e.g. humans. In multi-step screening processes of the subject invention, a candidate compound or library of compounds is subjected to screening in a second in vivo model, e.g. a mouse model, following screening in the subject transgenic animal model. Following the initial screening in the non-mammalian transgenic animals of the subject invention, the positive compounds are then screened in non-human mammalian animal models, including transgenic non-human mammalian animal models. Transgenic mouse models of neoplastic diseases and methods for their use in screening assays are described in: U.S. Pat. Nos. 5,917,124; 5,907,078; 5,849,996; 5,709,844; 5,550,316; and 4,736,866, the disclosures of which are herein incorporated by reference. In addition, a pre in vivo screening step may be employed, in which the compound is first subjected to an in vitro screening assay for its potential as a therapeutic agent in the treatment neoplastic conditions. Any convenient in vitro screening assay may be employed, where a variety of suitable in vitro screening assays are known to those of skill in the art.

Figure 5:
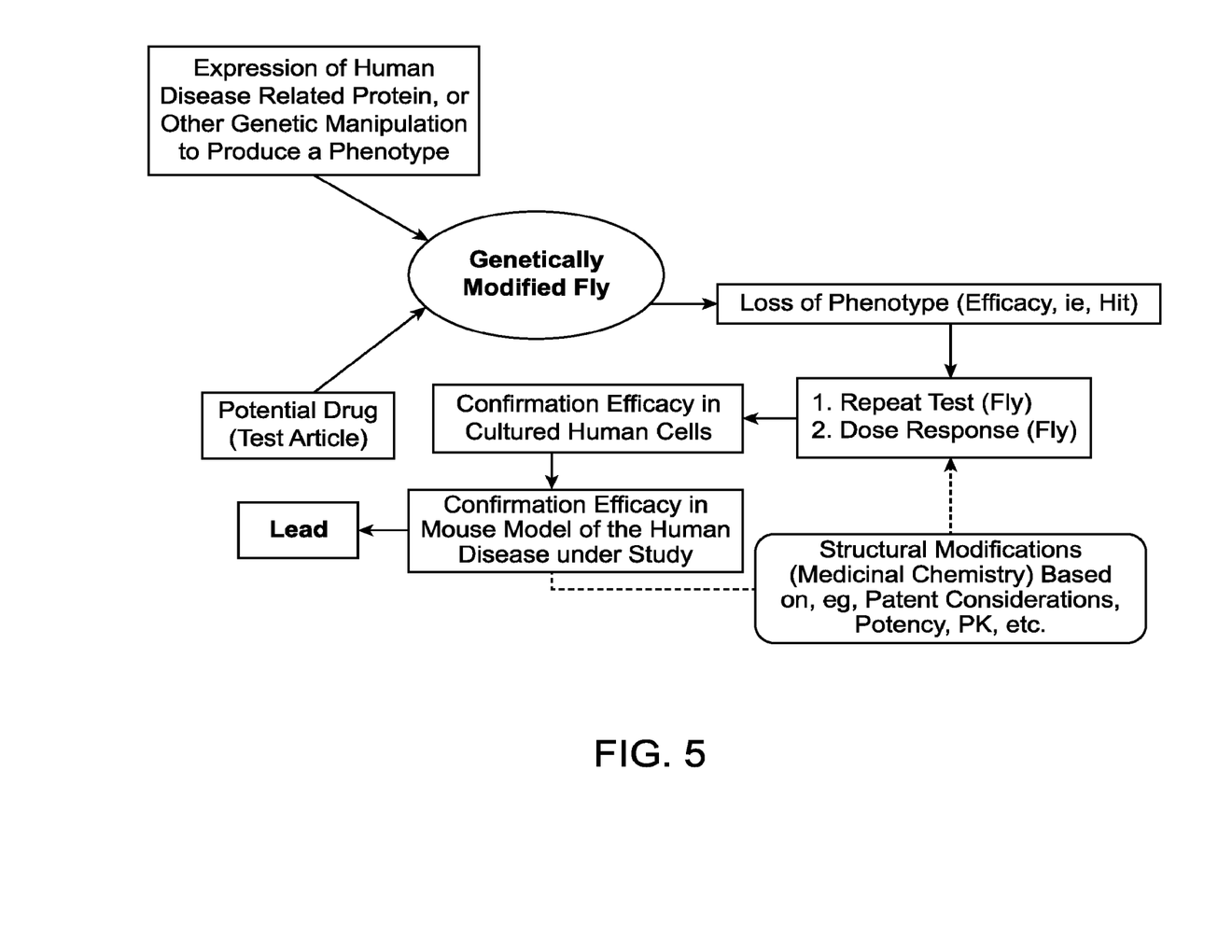
FIG. 5. A diagram illustrating a drug screening protocol using genetically modified flies according to an embodiment of the invention.
Figure 6:
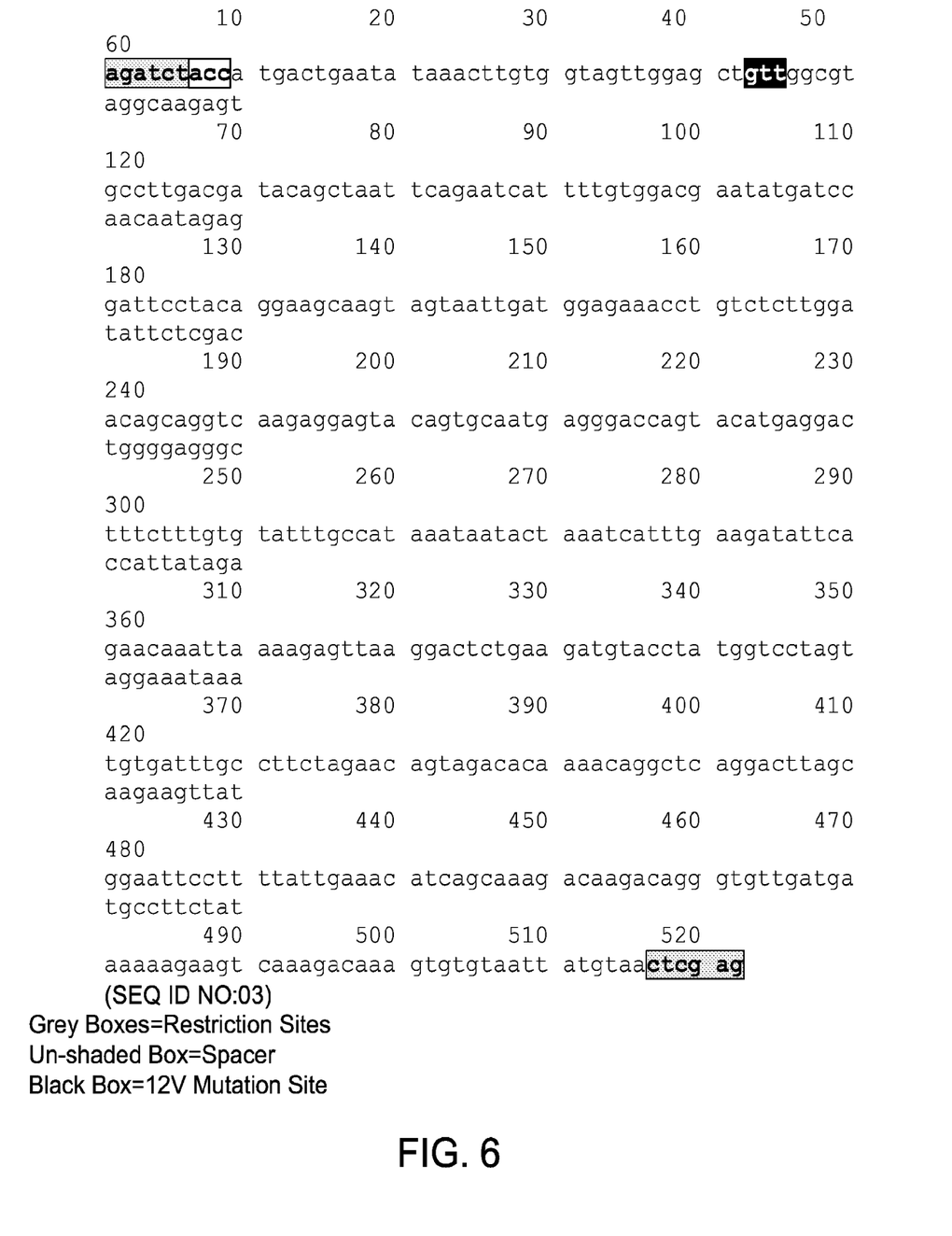
FIG. 6. 12V human kras gene.
Figure 7:
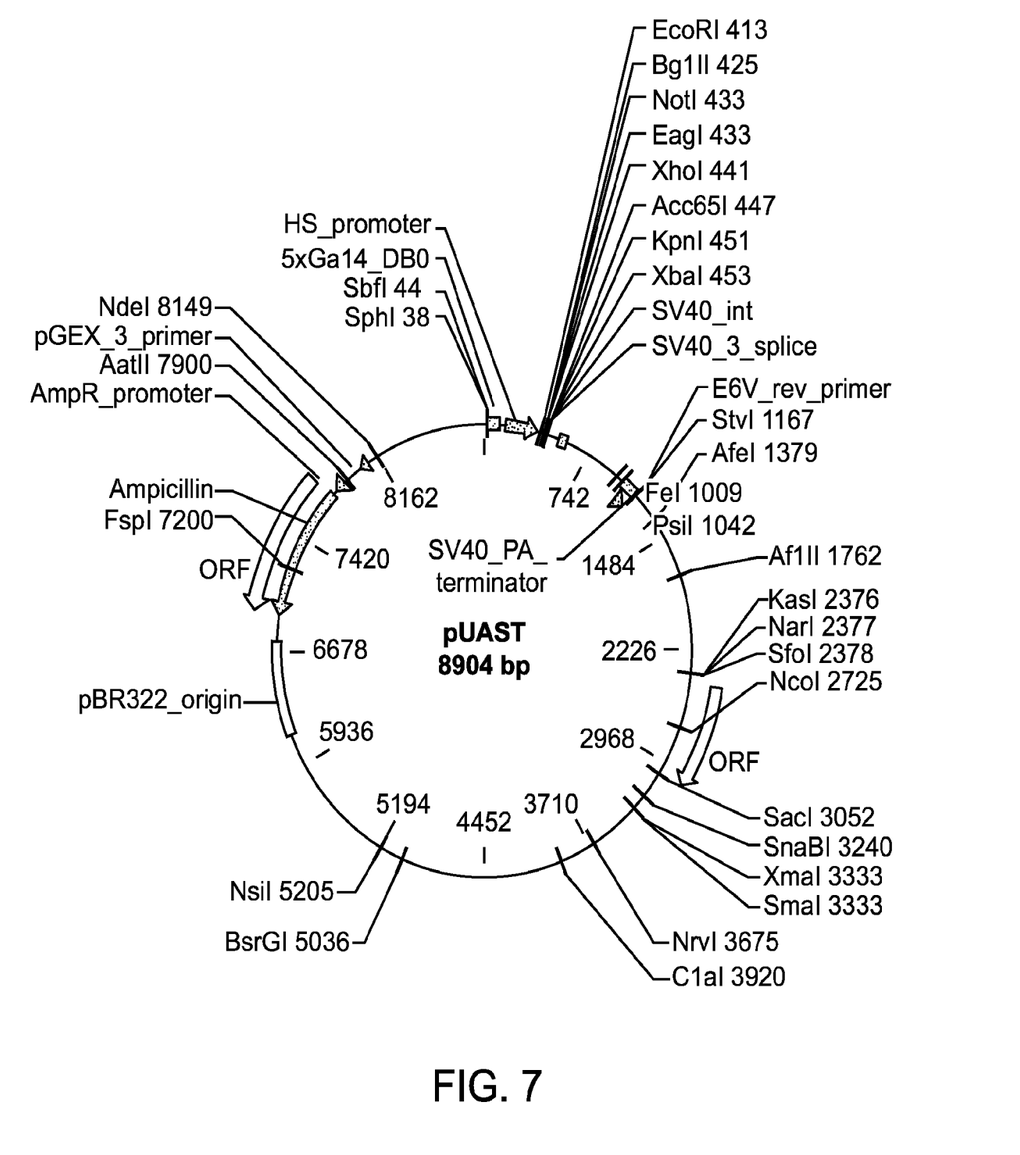
FIG. 7. pUAST map showing location of Bgl II and Xho I sites.

An example of a screening protocol employing transgenic flies according to embodiments of the invention is Illustrated in FIG. 5. Note that the screens rely on producing a phenotype in the fly after the introduction of the disease or untoward condition associated genes. The genetically manipulated fly is then exposed to libraries of chemical or other factors looking for a reversal of the phenotype. The chemicals or other factors that block the phenotype ("hits") are then tested in more traditional cell culture-based assays, and, if active in cell culture, the hits will be further examined in rodent models of the particular disease under study. Additional structural modifications are often also performed on hits that also are active in the cell culture and rodent models in order to improve the performance of the hit in these models. Screening in flies has the promise to lead to better drug candidates against promising therapeutic targets.

Also provided by the subject invention are therapeutic agents for use in treating a neoplastic condition, as well as pharmaceutical formulations thereof. The therapeutic agents of the subject invention are those agents identified using the screening methods described supra that show beneficial activity with respect to a neoplastic condition (or agents known to have an effect on the expression of a gene identified as modulating the phenotype of a neoplastic condition, where identification employs the use of the subject non-transgenic animals). Besides directly treating a neoplastic condition, therapeutic agents identified as described herein can also be used in combination with other agents, e.g such as anti-EGF therapy effective (Webster, et al., "kRAS testing and epidermal growth factor receptor inhibitor treatment for colorectal cancer in community settings", Cancer Epidemiol Biomarkers Prev (2013) 22:91-101.), to make such agents more effective. The use of the therapeutic agents from the subject invention can also be guided by analytical measurements to determine the genotype of the mutated kRAS associated with the patient administered the treatment. (Anderson, "Laboratory methods for KRAS mutation analysis", Expert Rev Mol Diagn. (2011) 11:635-642.)

Also provided are pharmaceutical compositions of the subject therapeutic agents. In the pharmaceutical compositions or formulations of the subject invention, agents described above are formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols. In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethyicellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Where the agent is a polypeptide, polynucleotide, analog or mimetic thereof (as identified using the mutant screen analysis protocols described supra, it may be introduced into tissues or host cells by any number of routes, including viral infection, microinjection, or fusion of vesicles. Jet injection may also be used for intramuscular administration, as described by Furth et al. (1992), *Anal Biochem* 205:365-368. The DNA may be coated onto gold microparticles, and delivered intradermally by a particle bombardment device, or "gene gun" as described in the literature (see, for example, Tang et al. (1992), *Nature* 356:152-154), where gold microprojectiles are coated with the DNA, then bombarded into skin cells.

Those of skill in the art will readily appreciate that dose levels can vary as a function of the specific compound, the severity of the symptoms and the susceptibility of the subject to side effects. Preferred dosages for a given compound are readily determinable by those of skill in the art by a variety of means.

Kits with unit doses of the active agent, usually in oral or Injectable doses, are provided. In such kits, in addition to the containers containing the unit doses will be an informational package insert describing the use and attendant benefits of the drugs in treating pathological condition of interest. Preferred compounds and unit doses are those described herein above.

Also provided are methods of treating cellular proliferative disease conditions, particularly neoplastic disease conditions, using the subject active agents. In the subject methods, an effective amount of the active agent of the subject invention is administered to the host to be treated. By "effective amount" is meant a dosage sufficient to produce a desired result, where the desired result is generally an amelioration or alleviation, if not complete cessation, of one or more symptoms of the cellular proliferative disease being treated. Administration of the agents can be achieved in various ways, including oral, buccal, rectal, parenteral, intraperitoneal, intradermal, transdermal, intracheal, etc. A variety of hosts are treatable according to the subject methods. Generally such hosts are "mammals" or "mammalian," where these terms are used broadly to describe organisms which are within the class mammalia, including the orders carnivore (e.g., dogs and cats), rodentla (e.g., mice, guinea pigs, and rats), and primates (e.g., humans, chimpanzees, and monkeys). In many embodiments, the hosts will be humans.

The following examples are offered by way of illustration and not by way of limitation.

EXPERIMENTAL

Example 1

Synthesis of Mutated Human kRAS Inserted into the pUAST Vector

To make this vector, the human kras-12V gene from Genecopia (Rockville, Md.) was digested with Bgl II and Xho I, and the Bgl II-Xho I fragment from the kras-12V shuttle vector inserted into the pUAST vector.

Bgl II and Xho I enzymes were purchased from New England BioLabs (NEB/Ipswich, Mass.), catalog numbers R0143 and R0146, respectively. The pUAST vector was a gift from Dr. Michele Calos, Stanford University (Palo Alto, Calif.). The plasmid from Genecopia and the pUAST vectors were individually digested with the enzymes from NEB for 4 hours at 37° C. in NEB buffer number 3.1. The digest products were separated on a horizontal 1% agarose gel, and purified using a Promega (Fitchburg, Wis.) gel purification kit, catalog number A281. The sizes of the isolated DNA were 8893 bp and 582 bp for the pUAST and kras fragments, respectively.

T4 DNA ligase from NEB was used to connect the DNA fragments in T4 DNA ligase buffer also from NEB. The ligated mixture was transformed into *E. Coli* and plated on LB-AMP plates. Ampicillin resistant colonies were picked into 2 mL LB and Promega (Fitchburg, Wis.) Wizard® minipreps (kit number A1330) performed. Isolates from the minipreps were analyzed at Sequetech (Mountain View, Calif.) to confirm insertion of the correct kRAS-12V sequence into the pUAST vector.

DNA for the kras-12V in pUAST was sent to BestGene (Chino, Calif.) for embryo injection and selection of the kRAS fly.

Example 2

Production of Muted kRAS/Cyo Fly

The pUAST-12V kras plasmid described in Example 1, was sent to BestGene, Inc. (Chino, Calif.) for transformation into the fly genome. The *Drosophila* background was $w^{118}$. Personnel at BestGene Inc. recovered transgenic adult flies with mutated kras inserted on the first, second, and third chromosomes respectively. Each of the individual transgenic lines was delivered to Tosk as balanced stocks.

About 200 embryos were injected and reared to adulthood (designated Generation 0, ie, G0, flies). About 140 G0 larvae were hatched and about 120 adults were pupated. Approximately 100 of these G0 adults were crossed to $5 \times w^{1118}$ flies, ie, $1 \times$G0 male crossed to $5 \times w^{1118}$ virgins and $1 \times$G0 female crossed with 5×w$^{1118}$ males (approximately 100 vials of crosses). About 80 of the above crosses were fertile and produced G1 flies. Each of the 80 crosses produced approximately 300 individual G1 flies in their single vials.

Each vial was inspected for G1 transformant founders. If found, the G1 transformant founder (G2) was crossed again (this is the transformant line). If there was a second transformant ("G1 siblings") in the same vial, it was kept as backup in case the initial GI transformant died. This process was repeated until all crosses were finished, or a 10th G1 transformants was found.

Three individual crosses for each of the founders were performed with the following balancer strains: (1) FM7i/XX with attached X, (2) CyO/Sco and (3) TM3 tb/TM6B sb. The resulting G3 adults were self-crossed (red eyed and with the proper balancer phenotype). Only the one cross that was successfully balanced for each original founder was kept. Furthermore, kRAS/kRAS flies were isolated from the original kRAS/CyO stock, breed and utilized in subsequent kRAS/kRAS x MS1096 to produce progeny expressing the mutant phenotype.

Example 3

Production of Mutated kRAS/kRAS x MS1096 Fly

The pUAST construct in the UAS kRAS fly possessed a UAS enhancer element. Binding of the GAL4 transcription factor to the UAS element induced expression of genes downstream of UAS. Crossing Drosophila adults that express GAL4 in specific tissues to the pUAST-kRAS transformant induced a strong kRAS expression in the same tissues that express GAL4.

MS1096 was purchased from the Drosophila stock center in Bloomington, Ind. (stock number 8860). MS1096 expresses GAL4 in the Drosophila wing and therefore only drives expression of oncogenic kRAS in the Drosophila wing.

Approximately 25 male mutated kRAS flies and approximately 25 MS1096 females were placed in a 250 mL polystyrene flask (VWR, Radnor, Pa., catalog number 16004-084) equipped with a stopper (VWR, catalog number 89140-960). The bottom of the flask was charged with approximately 10 g grape agar prepared using a published protocol.[1] Fifty embryos were transferred using forceps into glass vials (VWR, catalog number 89092-720) equipped with a stopper (VWR, catalog number 89168-886). The bottom of the vial was charged with approximately ½ teaspoon blue fly food from Carolina Biological Supply (Burlington, N.C.), catalogue number 173216.

[1] Sullivan W, Ashburner M, Hawley, S R, Drosophila Protocols 2000, Cold Spring Harbor Laboratory Press, p 544.

Figure 8:
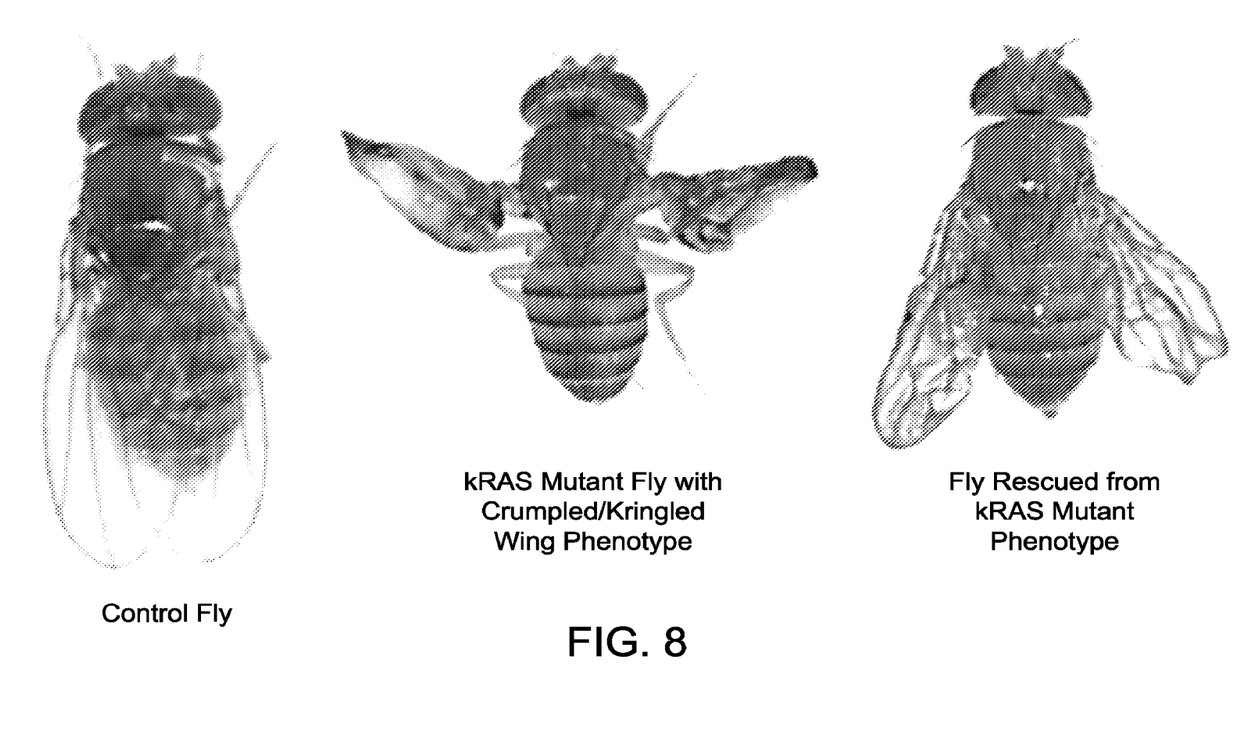
FIG. 8. Pictures of a control (GAL4 only) fly, a kRAS mutated (G12V) fly and a fly rescued from the kRAS/IkRAS x MS1096 GAL4 mutant F1 phenotypic with a deltarasin analog dissolved in DMSO.

After 14 days, the flies were examined for defective wings. Typical examples of wings with the mutated kRAS phenotype are shown in FIG. 8. The wing is crumpled/kringled and non-functional.

Example 4

Screening for Drugs that Reverse the Wing Phenotype of the Mutated kRAS/kRAS x MS1096 Fly Male mutated kRAS/kRAS flies were bred overnight with female MS1096/GAL4 flies in a fly condo[2] with a grape agar plate floor. The resulting embryos were gently dislodged from the grape agar plate using a squirt bottle containing 0.7% NaCl, 0.03% Triton X-100 In distilled water. The embryos were counted and then dissolved in a solution containing 14.4% sucrose, 0.7% NaCl and 0.05% Triton to give a concentration of 15 embryos/10 µL of solution.

[2] Sullivan W, Ashburner M, Hawley, S R, Drosophila Protocols 2000, Cold Spring Harbor Laboratory Press, pp 541-551.

The test article, 1-benzyl-2-phenyl-1H-benzo[d]imidazole which is a deltarasin analog with activity againsy RAS signaling,[1] was dissolved in DMSO to give a concentration of 10 mM. The deltarasin analog inhibitor was synthesized at the Tosk facility. Four µL of this solution, 100 µL of the embryo solution (150 embryos), ½ teaspoon blue fly food (North Carolina, catalogue number 173216) and 4 ml of water were combined in a vial (VWR, catalogue number 89092-720) and capped (VWR, catalogue number 89168-886). Using the recipe provided above, the final concentration of test article in the mixture was 10 µM.

The vials were placed in a 25° C. incubator for 14 days after which they. were examined for the percentage of flies with crumpled/kringled wings. A typical result for a fly rescued by treatment with the test article is provided in the FIG. 8 below. The wing of the fly significantly less crumpled/kringled although still non-functional. The goal for screening chemicals for anti-kRAS activity is to achieve in the kRAS mutant fly the rescue from the crumpled/kringled wing phenotype achieved with the deltarasin analog.

As can be seen from the above results, a known compound having antineoplastic activity also demonstrate antineoplastic activity in the subject mutant animals. The above results validate the claimed mutant animals as a screening models for agents with antineoplastic activity.

Table 1 below compares the typical appearance of wings from the control files, the kRAS mutant fly and flies rescued by treatment with a test article.

TABLE 1

Comparison of the Typical Appearance of Wings from Control Flies, kRAS Mutant Flies and Flies Rescued by Treatment with a Test Article

| Control | kRAS Mutant | Rescued |
| --- | --- | --- |
| Large, smooth flat wings | Smaller, deformed (crinkled) wings | Medium, semi-flat, less crinkled wings |
| Normal wing "veins" | Aberrant, disturbed wing "veins" with region clear of veins | Slightly aberrant wing "veins." Vein-free region is considerably smaller than same regions in kRAS mutant flies |
| Transparent wings | Translucent wings | Slightly translucent wings |
| Large, smooth flat wings | Smaller, deformed (crinkled) wings | Medium, semi-flat and less crinkled wings |
| Wings are parallel to body | Wings are stiffer and tend to be | Wings tend to be parallel to the fly |

TABLE 1-continued

Comparison of the Typical Appearance of Wings from Control Flies, kRAS
Mutant Flies and Flies Rescued by Treatment with a Test Article

| Control | kRAS Mutant | Rescued |
|---|---|---|
| in idle state | perpendicular to fly body | body |
| Able to take flight | Unable to take flight | Unable to take flight |

It is evident from the above results and discussion that the subject invention provides a valuable screening tool for use in the evaluation of potential therapeutic agents for use in the treatment of cellular proliferative disorders. Advantages of using the subject transgenic flies for screening potential therapeutic candidates include: adaptability of the subject flies to high throughput screening protocols, simplicity and low cost of maintaining the subject flies, ability of the subject flies to identify potentially orally active therapeutic agents, rapid reproduction of the subject flies, and ability of the subject flies to produce large numbers of offspring. Accordingly, the subject invention fills a void in the existing arsenal of screening tools, in that the subject invention provides a means for conducting in vivo high throughput screening assays. A further significant advantage is the ability to use the subject flies to identify compounds that exhibit low or no toxicity to normal dividing cells but still exhibit sufficient toxicity to abnormally dividing cells. As such, the subject screening methods provide a means for identifying effective anti-neoplastic agents that exhibit low or no toxicity to normal cells. Therefore, the subject invention represents a significant contribution to the art.

Notwithstanding the appended clauses, the disclosure is also defined by the following clauses:

1. A non-mammalian mutant animal, wherein said animal comprises a RAS transgene.
2. The non-mammalian mutant animal according to Clause 1, wherein the RAS transgene is a kRAS transgene.
3. The non-mammalian mutant animal according to Clause 2, wherein the kRAS transgene is a human kRAS transgene.
4. The non-mammalian mutant animal according to Clause 3, wherein the human kRAS transgene comprises a substitution mutation.
5. The non-mammalian mutant animal according to Clause 1, wherein the animal is an invertebrate.
6. The non-mammalian mutant animal according to Clause 5, wherein the invertebrate is an insect.
7. The non-mammalian mutant animal according to Clause 6, wherein the insect is a fly.
8. The non-mammalian mutant animal according to Clause 8, wherein the fly is a member of the family Drosophilidae.
9. The non-mammalian mutant animal according to Clause 8, wherein the fly is a *Drosophila melanogaster*.
10. The non-mammalian mutant animal according to Clause 1, wherein the transgene is ubiquitously expressed.
11. The non-mammalian mutant animal according to Clause 1, wherein the transgene is expressed in a tissue specific manner.
12. The non-mammalian mutant animal according to Clause 11, wherein the transgene is expressed in wing-tissue.
13. The non-mammalian mutant animal according to Clause 1, wherein the transgene is expressed in a developmental specific manner.
14. A transgenic *Drosophila melanogaster* comprising a kRAS transgene that is expressed in a tissue and developmentally specific manner sufficient to manifest as a non-lethal adult phenotype.
15. The transgenic *Drosophila melanogaster* according to Clause 14, wherein the non-lethal adult phenotype comprises a crimped wing.
16. The transgenic *Drosophila melanogaster* according to Clause 14, wherein the kRAS transgene encodes a mutant kRAS protein.
17. The transgenic *Drosophila melanogaster* according to Clause 16, wherein the mutant kRAS protein comprises a point mutation.
18. The transgenic *Drosophila melanogaster* according to Clause 17, wherein the point mutation comprises a G12 mutation.
19. The transgenic *Drosophila melanogaster* according to Clause 17, wherein the point mutation is selected from the group consisting of G12V, G13D and Q61L.
20. A method of screening a compound for activity with respect to a cellular proliferative disease, the method comprising:
   administering the compound to a non-mammalian transgenic animal according to any of Clauses 1 to 19; and
   observing the effect of the compound on the non-mammalian transgenic animal.
21. The method according to Clause 20, wherein the compound is orally administered to the non-mammalian transgenic animal.
22. The method according to Clause 21, wherein the compound is administered in a nutrient medium.
23. The method according to Clause 21, wherein the non-mammalian transgenic animal is at a juvenile development stage when the compound is orally administered.
24. The method according to Clause 23, wherein the non-mammalian transgenic animal is at an adult development stage when the animal is observed for the effect of the compound.
25. The method according to Clause 20, wherein the cellular proliferative disease is a neoplastic disease.
26. The method according to Clause 25, wherein the neoplastic disease is mediate by a kRAS mutation.
27. The method according to any of Clauses 20 to 26, wherein the method comprises:
   feeding a plurality of compounds to a plurality of non-mammalian transgenic animals in a manner sufficient to ensure that each animal is fed only a single type compound from the plurality of compounds; and
   observing the effect of said compounds on the plurality of animals.
28. The method according to any of Clauses 20 to 27, wherein the method further comprises further evaluating a compound observed to have activity in a subsequent activity assay.
29. The method according to Clause 28, wherein the subsequent activity assay is an in vitro assay.

30. The method according to Clause 28, wherein the subsequent activity assay is an in vivo assay.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely Illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is Intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A mutant fly model for neoplastic disease, wherein said fly is a member of the family *Drosophilidae* and comprises:
    (a) a stably integrated human kRAS transgene operatively linked to an upstream activator sequence (UAS); and
    (b) a GAL4 transactivator protein expressed specifically in wing-tissue of the fly; wherein the GAL4 transactivator protein binds to the UAS and induces expression of a constitutively active kRAS protein in a manner sufficient to manifest as an observable non-lethal adult phenotype in the wing of the fly, wherein the observable non-lethal adult phenotype is selected from crimped wing, translucent wing, inability to take flight, incomplete wing, aberrant wing vein and stiff wing.

2. The mutant fly model according to claim 1, wherein the fly is a *Drosophila melanogaster*.

3. A method of screening a compound for modulatory activity with respect to a cellular proliferative disease, the method comprising:
    administering the compound to the mutant fly model according to claim 1; and
    comparing the observable phenotype of the wings of a test fly administered the compound with the observable phenotype of the wings of a control mutant fly not administered the compound; and
    when the compound exacerbates or ameliorates the observable phenotype of the wings of the test fly as compared to the control fly, identifying the compound as having modulatory activity.

4. The method according to claim 3, wherein the method further comprises:
    testing a plurality of compounds in parallel by feeding the compounds to a plurality of the mutant flies in a manner sufficient to ensure that each fly is fed only a single type compound from the plurality of compounds; and
    comparing the observable phenotype of the wings of each test fly in the plurality of flies fed the single type of compound with the observable phenotype of the wings of a control fly not fed the compound; and
    when a differential response in the observable phenotype in the wings of the test fly as compared to the control fly, the single type compound is identified as a compound for further study.

5. The mutant fly model according to claim 1, wherein the human kRAS transgene further comprises a point mutation selected from G12X, G13D and Q61L.

6. The mutant fly model according to claim 1, wherein the human kRAS transgene is operatively linked to a UAS and the fly expresses a transactivator controlled by an endogenous wing-tissue specific promoter.

7. The mutant fly model according to claim 6, wherein the mutant fly is a mutated MS1096 fly.

8. The mutant fly model according to claim 7, wherein the fly has the genotype UAS-human kRAS$^{v12}$/UAS-human kRAS$^{v12}$ X MS1096-GAL4.

9. The A mutant fly model for neoplastic disease, wherein said fly is a member of the family *Drosophilidae* and comprises:
    (a) a stably integrated human kRAS transgene operatively linked to an upstream activator sequence (UAS); and
    (b) a GAL4 transactivator protein expressed specifically in wing-tissue of the fly; wherein the GAL4 transactivator protein binds to the UAS and induces expression of a constitutively active kRAS protein in a manner sufficient to manifest as an observable non-lethal adult phenotype in the wing of the fly, wherein the fly has the genotype UAS-human kRAS$^{v12}$/UAS-human kRAS$^{v12}$ X MS1096-GAL4 and wherein the observable phenotype is selected from crimped wing and incomplete wing.

10. The mutant fly model of claim 9, wherein the observable phenotype is crimped wing.

* * * * *